(12) United States Patent
Shalyaev et al.

(10) Patent No.: US 6,753,288 B2
(45) Date of Patent: Jun. 22, 2004

(54) OXIDATIVE CARBONYLATION OF HYDROXYAROMATIC COMPOUNDS

(75) Inventors: Kirill Vladimirovich Shalyaev, Clifton Park, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 55 days.

(21) Appl. No.: 10/163,824

(22) Filed: Jun. 6, 2002

(65) Prior Publication Data

US 2003/0032830 A1 Feb. 13, 2003

Related U.S. Application Data

(62) Division of application No. 09/699,829, filed on Oct. 30, 2000, now Pat. No. 6,462,217.

(51) Int. Cl.[7] .................. B01J 31/00; B01J 37/00; C08F 4/02; C08F 4/60

(52) U.S. Cl. ............... 502/155; 502/102; 502/154; 502/164; 502/168; 502/169; 502/170

(58) Field of Search ................. 502/102, 154, 502/155, 164, 168, 169, 170; 558/271, 274, 277

(56) References Cited

U.S. PATENT DOCUMENTS

| | | | |
|---|---|---|---|
| 3,329,665 A | | 7/1967 | Bessant et al. |
| 4,187,242 A | | 2/1980 | Chalk |
| 5,008,333 A | * | 4/1991 | Yates, III et al. ............ 525/92 |
| 5,231,210 A | | 7/1993 | Joyce et al. |
| 5,235,087 A | | 8/1993 | Klausener et al. |
| 5,239,106 A | | 8/1993 | Shafer |
| 5,284,964 A | | 2/1994 | Pressman et al. |
| 5,312,955 A | | 5/1994 | Pressman et al. |
| 5,373,083 A | | 12/1994 | King et al. |
| 5,380,907 A | | 1/1995 | Mizukami et al. |
| 5,399,734 A | | 3/1995 | King, Jr. et al. |
| 5,498,789 A | | 3/1996 | Takagi et al. |
| 5,502,232 A | | 3/1996 | Buysch et al. |
| 5,543,547 A | | 8/1996 | Iwane et al. |
| 5,625,091 A | | 4/1997 | Buysch et al. |
| 5,633,319 A | * | 5/1997 | Silvi et al. ............ 525/133 |
| 5,726,340 A | | 3/1998 | Takagi et al. |
| 5,760,272 A | | 6/1998 | Pressman et al. |
| 5,821,377 A | | 10/1998 | Buysch et al. |
| 5,856,554 A | | 1/1999 | Buysch et al. |
| 5,917,077 A | | 6/1999 | Chaudhari et al. |
| 6,114,564 A | | 9/2000 | Pressman et al. |
| 6,172,254 B1 | | 1/2001 | Pressman et al. |
| 6,180,812 B1 | | 1/2001 | Johnson et al. |
| 6,204,313 B1 | * | 3/2001 | Bastiaens et al. ............ 524/100 |
| 6,215,015 B1 | * | 4/2001 | Patel et al. ............ 558/274 |
| 6,221,939 B1 | * | 4/2001 | Campbell et al. ............ 524/117 |
| 6,245,929 B1 | * | 6/2001 | Soloveichik et al. ........ 558/274 |
| 6,265,340 B1 | * | 6/2001 | Johnson et al. ............ 502/122 |
| 6,310,229 B1 | * | 10/2001 | Soloveichik et al. ......... 556/83 |
| 6,407,279 B1 | * | 6/2002 | Buchanan et al. .......... 558/277 |
| 6,462,217 B1 | * | 10/2002 | Shalyaev et al. ............ 558/274 |
| 2003/0032830 A1 | * | 2/2003 | Shalyaev et al. ............ 558/274 |

FOREIGN PATENT DOCUMENTS

| | | |
|---|---|---|
| EP | 071286 | 2/1983 |
| EP | 0 350 700 | * 1/1990 |
| EP | 0663388 | 7/1995 |
| EP | 736325 | 3/1996 |
| GB | 1102566 | 2/1968 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 10-158221 | 6/1998 |
| JP | 10-316627 | 12/1998 |
| WO | WO 94/23836 | 10/1994 |

OTHER PUBLICATIONS

"Comprehensive Organometallic Chemistry", vol. 2, G. Wilkinson, ef. Pergamon Press, 1982, pp. 629, 6931, 654, 657, 662.*
US 2003/ A, US Pre–Grant publication to Shalyaev et al., Published Feb. 2003.*
Application Ser. No. 09/383,424, filed Aug. 27, 1999; "Catalyst Composition and Method for Producing Diaryl Carbonates", Bruce Fletcher Johnson et al.
International Search Report PCT/US 01/22358.

* cited by examiner

Primary Examiner—Mark L. Bell
Assistant Examiner—J. Pasterczyk
(74) Attorney, Agent, or Firm—Andrew J. Caruso; Patrick K. Patnode

(57) ABSTRACT

Organolead compounds such as tetraethyllead are useful in catalyst compositions for the oxidative carbonylation of hydroxyaromatic compounds to diaryl carbonates. They are employed in combination with a Group 8, 9, or 10 metal such as palladium, or a compound thereof, and a bromide or chloride such as tetraethylammonium bromide.

12 Claims, No Drawings

OXIDATIVE CARBONYLATION OF HYDROXYAROMATIC COMPOUNDS

This application is a division of application Ser. No. 09/699,829, filed Oct. 30, 2000, now U.S. Pat. No. 6,462,217, which is hereby incorporated by reference in its entirety.

BACKGROUND OF THE INVENTION

This invention relates to the preparation of diaryl carbonates, and more particularly to their preparation using a catalyst system having improved homogeneity.

Diaryl carbonates are valuable intermediates for the preparation of polycarbonates, for example by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst comprises a Group 8, 9, or 10 metal having an atomic number of at least 44 (hereinafter "heavy transition metals"), said metals consisting of ruthenium, rhodium, palladium, osmium, iridium and platinum, or a complex thereof.

The production of carbonates may frequently be improved by including a lead-containing cocatalyst along with the heavy transition metal catalyst. Suitable lead-containing cocatalysts have been described broadly in various patents and publications, particularly in U.S. Pat. No. 5,498,789, which is incorporated herein by reference. Also required in general is the use of various halides, as illustrated by tetra-n-butylammonium bromide or chloride, as part of the catalyst package. Compounds characterized as inert solvents, such as toluene, diethyl ether, diphenyl ether and acetonitrile, can also be present.

The presence in the catalyst composition of lead compounds such as lead(II) oxide or lead(II) alkoxides or phenoxides, conventionally used as lead sources, frequently introduces problems of various kinds. Such compounds may interact with other materials present and frequently form precipitates. These precipitates, of variable composition, introduce irreproducibility into the carbonylation reaction and unpredictably affect yield and/or selectivity. They also adversely affect isolation and purification of the diaryl carbonate and impair recycle of catalyst constituents.

It is of interest, therefore, to develop improved methods of delivering lead to the carbonylation catalyst system.

SUMMARY OF THE INVENTION

The present invention provides lead-containing catalyst systems of improved properties, including an increase in homogeneity and in predictability of catalytic results.

In one of its aspects, the invention is a method for preparing a diaryl carbonate which comprises contacting at least one hydroxyaromatic compound with oxygen and carbon monoxide in the presence of an amount effective for carbonylation of a catalyst composition comprising the following and any reaction products thereof:

(A) a Group 8, 9, or 10 metal having an atomic number of at least 44 or a compound thereof, (B) at least one bromide or chloride salt, and (C) at least one lead compound having direct lead-carbon linkages.

Another aspect of the invention is a catalyst composition comprising components A–C as defined above.

DETAILED DESCRIPTION; PREFERRED EMBODIMENTS

Any hydroxyaromatic compound may be employed in the method of the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonate oligomers.

Other essential reagents in the diaryl carbonate preparation method of the invention are oxygen and carbon monoxide, which react with the phenol to form the desired diaryl carbonate. They may be employed in high purity form or diluted with another gas such as nitrogen, argon or carbon dioxide which has no negative effect on the reaction.

For the sake of brevity, the constituents of the catalyst system of the invention are defined as "components" irrespective of whether a reaction between said constituents occurs before or during the carbonylation reaction. Thus, the catalyst system may include said components and any reaction products thereof.

Component A of the catalyst system is one of the heavy transition metals, preferably palladium, or a compound thereof. Thus, useful palladium materials include elemental palladium-containing entities such as palladium black, palladium/carbon, palladium/alumina and palladium/silica; palladium compounds such as palladium chloride, palladium bromide, palladium iodide, palladium sulfate, palladium nitrate, palladium acetate and palladium 2,4-pentanedionate; and palladium-containing complexes involving such compounds as carbon monoxide, amines, nitriles, phosphines and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate, especially the latter, are generally most preferred. Mixtures of the aforementioned palladium materials are also contemplated.

Component B is at least one bromide or chloride salt. It may be an alkali metal or alkaline earth metal bromide or chloride, preferably a bromide such as lithium bromide, sodium bromide, potassium bromide, calcium bromide or magnesium bromide. It may also be an onium bromide or chloride, preferably a bromide, including trialkylamine hydrobromides and tetraalkylammonium, tetraalkylphosphonium, hexaalkylguanidinium, and sulphonium bromides. Illustrative examples include tetramethylammonium bromide, tetraethylammonium bromide or tetra-n-butylammonium bromide; a tetraalkylphosphonium salt such as tetramethylphosphonium bromide; or a hexaalkylguanidinium salt such as hexaethylguanidinium bromide. The bromides are often preferred, with tetraalkylammonium bromides being especially preferred.

Component C is at least one lead compound having at least one direct lead-carbon linkage; i.e., an organolead compound. Illustrative organolead compounds are tetraethyllead and tetraphenyllead. Tetraethyllead is, of course, commercially available and has been employed as an antiknock additive for motor fuels, especially gasoline, although, it is no longer employed for this purpose in the United States by reason of its toxicity.

The use of an organolead compound has significant advantages in improvement of homogeneity of the catalyst composition. Specifically, mixtures of organolead compound, phenol and ionic bromides or chlorides, preferably alkali metal or alkaline earth bromides or chlorides, or onium salts such as tetraalkylammonium and tetraalkylphosphonium bromides or chlorides are homogeneous, in contrast to similar mixtures containing lead(II) oxide, lead(II) alkoxides or lead(II) phenoxide. In preferred embodiments the ionic bromide or chloride is substantially soluble in hydroxyaromatic compound. In embodiments where substantial solubility of ionic bromide or chloride may not be obtained, then a co-solvent may be added, such as tetraglyme or other polyether as taught in U.S. Pat. No. 6,114,564 which is incorporated herein by reference.

It has also been discovered that an improvement in reaction rate can be achieved by pretreating the organolead compound with phenol in the presence of a tetraalkylammonium bromide, such pretreatment being performed at temperatures in the range of about 30–90° C. for at least about 8 hours and preferably for at least about 10 hours.

Other compounds may also be present in the catalyst composition. Compounds of cerium, cobalt, copper, titanium and manganese are particularly useful, with the 2,4-pentanedionates (the oxy-2,4-pentanedionate in the case of titanium) frequently being preferred.

In addition to the aforementioned reactants and catalyst system, it is strongly preferred for a desiccant to be present in the reaction system. The preferred desiccants are non-reactive materials such as molecular sieves, as illustrated by 3-Ångstrom (hereinafter "3A") molecular sieves. They are usually isolated from the other reactants, as by presence in a basket mounted to a stirrer shaft or the like.

Component A is most often present in the amount of about 0.1–10,000 ppm by weight of the appropriate Group 8, 9, or 10 metal (usually palladium), based on hydroxyaromatic compound, and component B in the amount of about 1–2,000 moles per gram-atom of the Group 8, 9, or 10 metal of component A. Component C is generally present in the amount of about 0.2–200 gram-atoms of lead per gram-atom of the Group 8, 9, or 10 metal of component A. Compounds of other metals, when present, will usually be at levels in the range of about 1–50 gram-atoms per gram-atom of the Group 8, 9, or 10 metal of component A.

The method of the invention is preferably conducted in a reactor in which the hydroxyaromatic compound and catalyst system are charged under pressure of carbon monoxide and oxygen and heated. The reaction pressure is most often within the range of about 1–500 and preferably about 1–150 atm. Gas is usually supplied in proportions of about 1–50 mole percent oxygen with the balance being carbon monoxide and optionally one or more inert gases, and in any event outside the explosion range for safety reasons. The gases may be introduced separately or as a mixture. Reaction temperatures in the range of about 60–150° C. are typical. It is often preferred to maintain a substantially constant gas pressure and partial pressure of carbon monoxide and oxygen until conversion of the hydroxyaromatic compound is complete, as described, for example, in U.S. Pat. No. 5,399,734, which is incorporated herein by reference.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 5,239,106 and 5,312,955, which are incorporated herein by reference.

The invention is illustrated by the following examples. All percentages are by weight unless otherwise designated. Minor variations in reagent amounts from one example to another are not believed significant from the standpoint of yield and selectivity of diphenyl carbonate.

EXAMPLES 1–14

Carbonylation experiments were conducted in small vials at a total volume of 25 microliters ($\mu$l), employing a catalyst system containing phenol, 25 millimoles (mmol) of palladium(II) 2,4-pentanedionate per mole of phenol and various proportions per equivalent of palladium of tetraethyllead, tetraethylammonium bromide ("TEAB") and (in certain examples) cerium(III) 2,4-pentanedionate, manganese(III) 2,4-pentanedionate or titanium(IV) oxide bis(2,4-pentanedionate).

Each vial was capped with a snap cap having a slit with a polytetrafluoroethylene septum and the vials were placed in an autoclave which was pressurized to 88.4 atmospheres (atm) with a mixture of 90 mole percent carbon monoxide and 10 mole percent oxygen and heated at 100° C. for 3 hours. The contents of the vials were analyzed for diphenyl carbonate by vapor phase chromatography.

The results are given in Table I, in comparison with controls employing lead(II) oxide in an equivalent amount in place of the tetraethyllead. Proportions of catalyst constituents are in gram-atoms ("g-a") of metal or equivalents ("eq") of bromide per gram-atom of palladium. TON, or turnover number, is the number of moles of aromatic carbonate produced per mole of palladium utilized.

TABLE I

| Example | Pb, g-a | Ce, g-a | Ti, g-a | Mn, g-a | TEAB, eq | TON | TON, control |
|---|---|---|---|---|---|---|---|
| 1 | 12 | — | — | — | 100 | 285 | 103 |
| 2 | 12 | — | — | — | 400 | 2,184 | 2,785 |
| 3 | 12 | — | — | — | 600 | 2,239 | 2,886 |
| 4 | 50 | — | — | — | 100 | 250 | 447 |
| 5 | 50 | — | — | — | 400 | 707 | 2,492 |
| 6 | 50 | — | — | — | 600 | 4,885 | 4,692 |
| 7 | 12 | 5.6 | — | — | 100 | 1,451 | 1,635 |
| 8 | 12 | 5.6 | — | — | 400 | 1,824 | 2,011 |
| 9 | 50 | 5.6 | — | — | 100 | 1,612 | 1,828 |
| 10 | 50 | 5.6 | — | — | 400 | 3,044 | 2,735 |
| 11 | 12 | — | 12 | — | 100 | 881 | 1,020 |
| 12 | 12 | — | 12 | — | 400 | 1,544 | 1,434 |
| 13 | 12 | — | — | 12 | 100 | 947 | 1,005 |
| 14 | 12 | — | — | 12 | 400 | 642 | 568 |

It is apparent that in most instances, catalyst compositions containing tetraethyllead performed comparably to and sometimes better than those containing lead(II) oxide.

EXAMPLES 15–18

The procedures of Examples 7–10 using 5.6 equivalents of cerium salt was repeated, replacing the TEAB on an equimolar basis with tetra-n-butylammonium chloride ("TBAC"). The results (without controls) are given in Table II.

TABLE II

| Example | Pb, g-a | TBAC, eq | TON |
|---|---|---|---|
| 15 | 12 | 400 | 877 |
| 16 | 12 | 600 | 785 |
| 17 | 50 | 400 | 2,001 |
| 18 | 50 | 600 | 2,509 |

It is apparent that the use of chlorides in place of bromides in the invention is also feasible.

EXAMPLE 19

A pressure-resistant reactor was charged with 60.2 grams (g) (640 mmol) of phenol, 4.5 milligrams (mg) (0.0148 mmol) palladium(II) 2,4-pentanedionate (25 ppm palladium based on phenol), 308.1 mg of tetraethyllead and 2.0146 g (9.59 mmol) of TEAB. 3A molecular sieves, 30 g, were placed in a perforated polytetrafluoroethylene basket mounted to the stir shaft of each reactor.

The reactor was sealed, pressurized to 91.2 atm with a mixture of 90.1% (by volume) carbon monoxide and 9.9% oxygen and heated over 10 minutes to 100° C., with stirring. Heating at this temperature and stirring were continued for five hours, with periodic sampling. The TON of diphenyl carbonate obtained was 4,367.

EXAMPLE 20

The procedure of Example 19 was repeated, except that the tetraethyllead was pretreated for 12 hours at 70° C. with the phenol in the presence of the TEAB. The TON of diphenyl carbonate obtained was 8,440, showing the advantage of pretreatment.

EXAMPLE 21

The procedure of Example 19 is repeated, except at an equimolar amount of sodium bromide is used in place of TEAB. The mixture also contains 6% by volume tetraglyme. A homogeneous solution is obtained. The solution is effective to provide oxidative carbonylation of phenol.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A catalyst composition for preparing diaryl carbonates from at least one hydroxyaromatic compound comprising the following and any reaction products thereof:
   (A) a Group 8, 9, or 10 metal having an atomic number of at least 44 or a compound thereof,
   (B) at least one bromide or chloride salt, and
   (C) at least one lead compound having at least one direct lead-carbon bond.

2. The composition according to claim 1 wherein the Group 8, 9, or 10 metal in component A is palladium.

3. The composition according to claim 2 wherein component A is palladium(II) 2,4pentanedionate.

4. The composition according to claim 1 wherein component B is a bromide salt.

5. The composition according to claim 4 wherein component B is an alkali metal or alkaline earth metal bromide, an onium bromide, a phosphonium bromide, a sulfonium bromide, a tetraalkylammonium bromide, a tetraalkylphosphonium bromide or a hexaalkylguanidinium bromide.

6. The composition according to claim 1 wherein a compound of cerium, cobalt, copper, titanium or manganese is also present in the catalyst composition.

7. The composition according to claim 6 wherein component A is present in the amount of about 0.1–10,000 ppm of Group 8, 9, or 10 metal based on hydroxyaromatic compound, component B in the amount of about 1–2,000 moles per gram-atom of the Group 8, 9, or 10 metal of component A, component C in the amount of about 0.2–200 gram-atoms of lead per gram-atom of the Group 8, 9, or 10 metal of component A and any compound of cerium, titanium or manganese in the amount of about 1–50 gram-atoms per gram-atom of the Group 8, 9, or 10 metal of component A.

8. A catalyst composition for preparing a diaryl carbonate from at least one hydroxyaromatic compound, the catalyst composition comprising the following and any reaction products thereof:
   (A) a Group 8, 9, or 10 metal having an atomic number of at least 44 or a compound thereof.
   (B) at least one bromide or chloride salt, and
   (C) at least one lead compound having at least one direct lead-carbon bond,
   wherein the catalyst composition is prepared by pretreating the at least one lead compound with at least one hydroxyaromatic compound in the presence of at least one bromide or chloride salt.

9. The catalyst composition according to claim 8 wherein the hydroxyaromatic compound is phenol.

10. The catalyst composition according to clam 8 wherein the pretreatment is performed at temperatures in the range of about 30–90° C. for at least about 8 hours.

11. A catalyst composition comprising the following and any reaction products thereof:
   (A) palladium or a compound thereof,
   (B) at least one tetraalkylammonium, tetraalkylphosphonium or hexaalkylguanidinium bromide or chloride, and
   (C) tetraethyllead or tetraphenyllead.

12. The catalyst composition of claim 11 prepared by pretreating tetraethyllead or tetraphenyllead with phenol in the presence of at least one tetraalkylammonium, tetraalkylphosphonium or hexaalkylguanidinium bromide or chloride before combining with palladium or a compound thereof.

* * * * *